(12) United States Patent
Körner

(10) Patent No.: US 12,186,239 B2
(45) Date of Patent: Jan. 7, 2025

(54) TEMPERATURE-REGULATING STRETCHER SUPPORT

(71) Applicant: Andreas Körner, Naundorf (DE)

(72) Inventor: Andreas Körner, Naundorf (DE)

( * ) Notice: Subject to any disclaimer, the term of this patent is extended or adjusted under 35 U.S.C. 154(b) by 958 days.

(21) Appl. No.: 16/979,004

(22) PCT Filed: Mar. 7, 2019

(86) PCT No.: PCT/EP2019/055740
§ 371 (c)(1),
(2) Date: Sep. 8, 2020

(87) PCT Pub. No.: WO2019/170816
PCT Pub. Date: Sep. 12, 2019

(65) Prior Publication Data
US 2021/0369514 A1    Dec. 2, 2021

(30) Foreign Application Priority Data

Mar. 9, 2018    (DE) ..................... 20 2018 101 328.9

(51) Int. Cl.
*A61G 1/04*    (2006.01)
*A61F 7/00*    (2006.01)
*A61F 7/08*    (2006.01)

(52) U.S. Cl.
CPC ............... *A61G 1/04* (2013.01); *A61F 7/007* (2013.01); *A61F 7/08* (2013.01);
(Continued)

(58) Field of Classification Search
CPC .. A61G 1/04; A61G 2210/90; A61G 2210/70; A61F 2007/0078; A61F 2007/0077; A61F 7/007; A61F 2007/008; A61F 2007/0081; A61F 2007/0082; A61F 2007/0086; A61F 2007/0098;
(Continued)

(56) References Cited

U.S. PATENT DOCUMENTS 5,626,151 A    5/1997    Linden
5,975,081 A    11/1999   Hood et al.
(Continued)

FOREIGN PATENT DOCUMENTS

CN    2731147 Y  * 10/2005
DE    87 03 704 U1    4/1987
(Continued)

OTHER PUBLICATIONS

International Search Report issued Jun. 19, 2019 in corresponding International Patent Application No. PCT/EP2019/055740, filed Mar. 7, 2019 (with English Translation.

*Primary Examiner* — David R Hare
*Assistant Examiner* — Deborah Talitha Gedeon
(74) *Attorney, Agent, or Firm* — Global IP Counselors, LLP

(57) ABSTRACT

A temperature-regulating support includes a head part and a body part that are coupled to one another, at least one temperature-regulating layer, and a support layer. The at least one temperature-regulating layer has a battery as a power supply. The battery is arranged in a compartment of the support, and the battery is capable of being removed from the compartment and can be inserted into the compartment.

19 Claims, 10 Drawing Sheets

(52) U.S. Cl.
CPC ............ *A61F 2007/0078* (2013.01); *A61F 2007/0086* (2013.01); *A61F 2007/0095* (2013.01); *A61G 2210/70* (2013.01); *A61G 2210/90* (2013.01)

(58) Field of Classification Search
CPC ............ A61F 7/0097; A61F 2007/009; H01M 50/20; H01M 50/202; H01M 50/2013; H01M 2220/20
See application file for complete search history.

(56) References Cited

U.S. PATENT DOCUMENTS

| | | | |
|---|---|---|---|
| 6,175,977 | B1 | 1/2001 | Schumacher et al. |
| 2004/0064885 | A1* | 4/2004 | Moster ................. A61G 7/0507 381/388 |
| 2006/0020311 | A1* | 1/2006 | Ellis ........................ A61F 7/007 607/96 |
| 2007/0157385 | A1* | 7/2007 | Lemire ............... A61M 5/1415 5/618 |
| 2009/0119834 | A1* | 5/2009 | Kneale .................. A61B 50/10 600/300 |
| 2013/0150928 | A1 | 6/2013 | Walter et al. |
| 2015/0088233 | A1 | 3/2015 | MacIntyre-Ellis |
| 2016/0158094 | A1 | 6/2016 | Lavigne |
| 2016/0331614 | A1* | 11/2016 | Furman ................. A61G 7/005 |
| 2017/0079733 | A1 | 3/2017 | Darrah et al. |
| 2017/0172829 | A1* | 6/2017 | Tessmer ............... A61G 7/0516 |
| 2019/0390851 | A1* | 12/2019 | Sun ........................... F21L 4/08 |

FOREIGN PATENT DOCUMENTS

| | | | |
|---|---|---|---|
| DE | 697 34 289 T2 | 7/2006 | |
| DE | 102006034923 A1 * | 1/2008 | ............ H05K 5/006 |
| DE | 102015007526 A1 * | 12/2016 | |
| WO | 2013/086540 A2 | 6/2013 | |

* cited by examiner

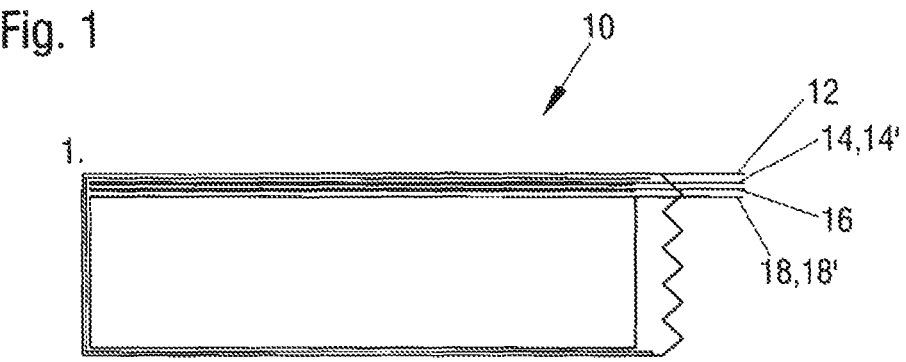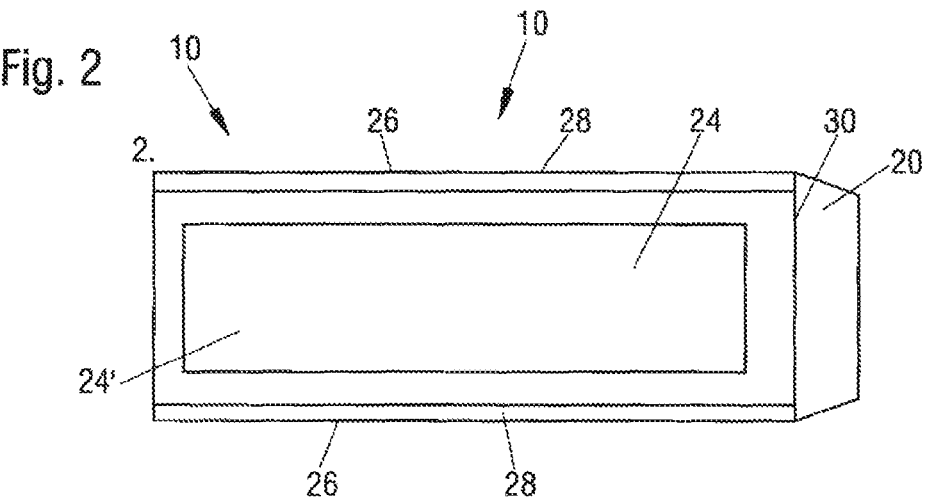

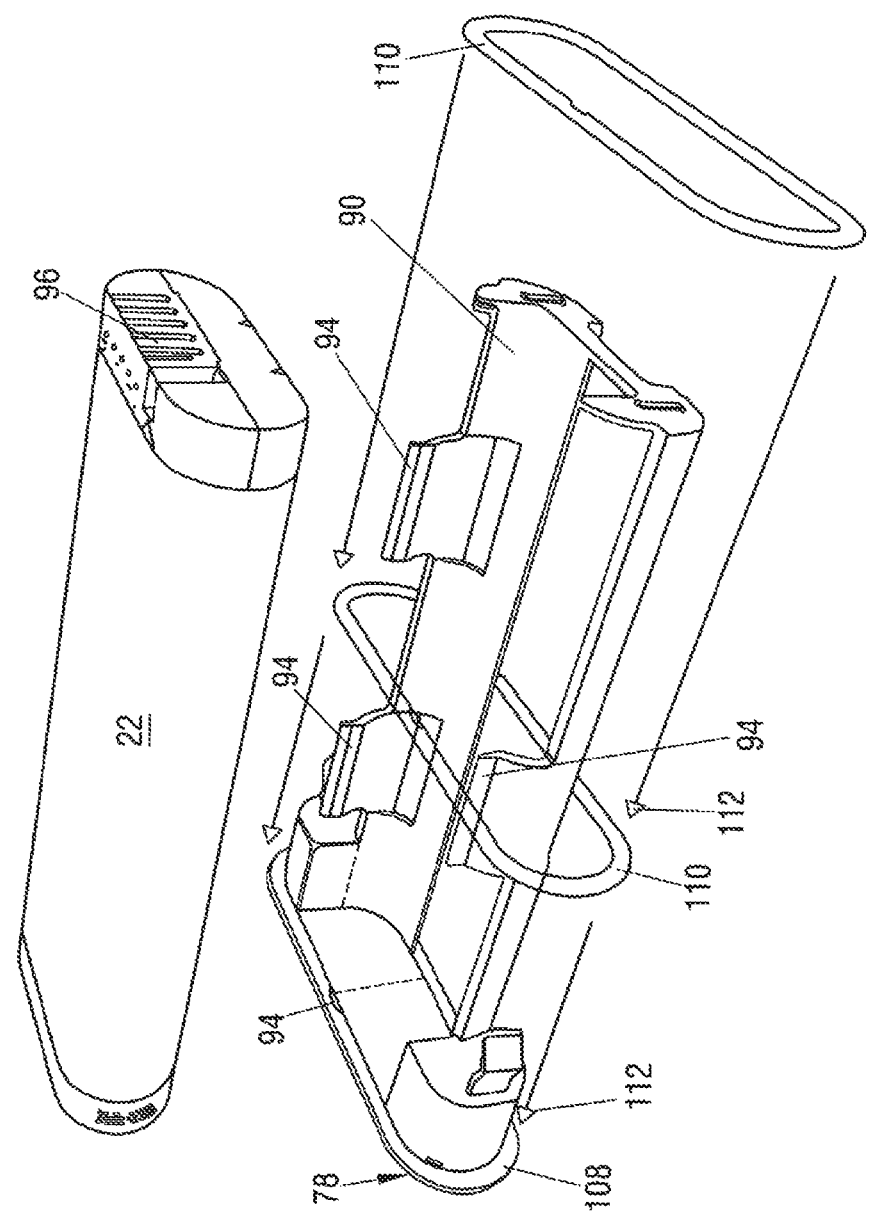

TEMPERATURE-REGULATING STRETCHER SUPPORT

CROSS-REFERENCE TO RELATED APPLICATION

This application is a U.S. National Stage application of International Application No. PCT/EP2019/055740, filed Mar. 7, 2019, which claims priority to German Patent Application No. 20 2018 101 328.9, filed Mar. 9, 2018, the contents of each of which are hereby incorporated herein by reference.

BACKGROUND

Field of the Invention

The present invention relates to a temperature-regulating stretcher support comprising a head part and a body part that are coupled to one another; at least one temperature-regulating layer; and a support layer.

Background Information

In medical emergencies, it is generally necessary to treat a patient quickly and efficiently. Various types of vehicles are used to transport patients to a hospital. In this respect, stretchers are used in the vehicles.

Currently, the most common stretcher supports are usually only suitable for use within vehicles or buildings and usually not for longer use outside vehicles and buildings.

Temperature-regulating stretcher supports are used to provide stretcher supports for mobile use outside vehicles. In emergency situations, it has been shown that patients can be helped by supplying cold or heat since e.g. the blood vessels can dilate due to the supply of heat. The blood flow is thereby stimulated and the muscles can relax. Due to the supply of heat, patients can also be helped after a medical emergency, for example an accident or an acute illness, by the supply of heat.

In contrast to this, the blood vessels contract on the supply of cold and the muscles can tense up. The exiting of blood, e.g. into surrounding tissue, can be prevented in this respect. By regulating the temperature to different temperatures, a patient can thus be treated in a more targeted manner outside medical facilities or inside or outside vehicles even in the case of very serious injuries.

SUMMARY

It has been found that one disadvantage of such temperature-regulating stretcher supports is that they are often cabled within the vehicle and can thus form a hazard zone in the vehicle. The service life of such stretcher supports can also be impaired by the cabling of such temperature-regulating stretcher supports.

It is an object of the present invention to provide an improved temperature-regulating stretcher support that has a longer life and that can be used without a cabling effort. It is a further object of the present invention to provide a stretcher support that makes it possible to minimize a space requirement within a vehicle.

This object is satisfied by a temperature-regulating support having the features described herein.

A temperature-regulating stretcher support of this kind such as, for example, a medical stretcher support comprises a head part and a body part that are coupled to one another; at least one temperature-regulating layer; and a support layer, wherein the at least one temperature-regulating layer has a battery as a power supply. The temperature-regulating stretcher support is characterized in that the battery is arranged in a compartment of the stretcher support; and in that the battery can be removed, preferably repeatedly, from the compartment and can be inserted into the compartment.

Due to the arrangement of the battery in a compartment of the stretcher support, both the battery and the electrical connection between the battery and the temperature-regulating layer can be better protected against external influences such as liquids or medical staff stumbling. By inserting and removing the battery, it can be charged in a cable-free manner, for example at a docking station, which simplifies the charging of the battery.

The support is generally used in the medical field during the transport of patients and can preferably be implemented as a stretcher support. There is also the possibility of integrating the support in a vacuum mattress or in a transport chair or hospital transport chair.

The compartment and the battery are preferably arranged in the head part of the stretcher support. The head part of a stretcher support is usually more rigid than the body part and thus provides improved protection of the battery against impacts and the like that can occur when the stretcher support is used.

The compartment particularly preferably has a covering, whereby the battery can additionally be protected against external influences.

The covering is preferably fixedly connected to an upper side of the stretcher support and is releasably connected to a lower side of the stretcher support. A disinfectant is typically applied over a large area on the upper side of the stretcher support on the cleaning of the stretcher support; a penetration of the disinfectant into the compartment from above can be better prevented by the fixed connection of the covering to the upper side. Due to the releasable connection to the lower side of the stretcher support, the compartment and thus the battery can be reached from the outside in a simple manner.

The stretcher support in particular comprises at least one magnetic device, in particular a magnet, at the lower side of the stretcher support that cooperates with a magnetic counter-piece at the covering.

The compartment is preferably adapted to the outer shape of the battery and the stretcher support, preferably the compartment, has a mechanism of means, for example latch noses preloaded by a spring or the like, for releasably holding the battery. The battery can thus be stored within the stretcher support in a simple manner.

The temperature-regulating layer can particularly preferably be regulated to an at least substantially constant temperature in the range from 15 to 42° C., preferably from 16 to 30° C., in particular from 20 to 30° C., specifically from 22 to 26° C., with the temperature being able to be set in dependence on the patient by an apparatus. These temperature ranges are perceived as pleasant by patients who are transported on the stretcher support and enable a heating or a cooling of the body of the patient.

The apparatus is preferably arranged at the stretcher support. The apparatus is thus provided in the direct vicinity of its place of installation. In this connection, it is in particular possible to arrange the apparatus at the head part of the stretcher support since this region of the stretcher support is the most easily accessible when a vehicle moves and is also better protected by the attachment to the rigid head part than to the body part of the stretcher support.

The apparatus is in particular arranged at a lug that is connected to the stretcher support, in particular to the head part. The presence of the temperature-regulating stretcher support can be made better visible by such a lug.

It is possible to arrange the apparatus at the battery to save construction space and the like.

The apparatus particularly preferably comprises a charge state display; an on/off button; a control panel for regulating the temperature; and/or a screen. Such operating elements or display elements simplify the use of the stretcher support. Thus, the temperature-regulating operation of the stretcher support that can be heated can, for example, be switched on or off in a simple manner in order e.g. to switch off the stretcher support during empty runs or during normal patient transport, whereby power can be saved. All the essential electrical components can thus be arranged in or at the stretcher support and a charge state of a battery can be visible from the outside.

The apparatus is preferably connected to the battery, to the temperature-regulating layer, and to a regulation circuit. In this respect, the power supply of all the electrical components of the stretcher support is guaranteed by one and the same battery.

The regulation circuit can in particular comprise a microcontroller that enables electrical signals that are provided at the stretcher support to be transmitted to further devices and/or to be evaluated.

The support and/or the battery is/are preferably configured, in particular by the regulation circuit, to output an acoustic and/or visual signal as soon as a predefined charge state threshold is undercut, in particular with the predefined charge state threshold corresponding to a charge state of less than 20%, preferably less than 10%, in particular less than 5%, of the battery. In this respect, it can be indicated to a user of the support that the battery has to be charged.

One or more sensors are preferably arranged in the stretcher support and are configured to detect patient-specific parameters. These sensors can detect the status parameters of the patient located on the stretcher support without additional sensors having to be attached to the patient from the outside, which considerably minimizes the cabling effort within the vehicle and simultaneously increases the range of use of the stretcher support.

One or more medical devices are preferably arranged in the stretcher support. They are in particular configured to treat the patient in dependence on the patient-specific parameters, for example, to resuscitate a patient by a defibrillator in the event of a recognized cardiac arrest. Such medical devices can preferably be configured to perform a treatment on a patient.

The microcontroller is particularly preferably configured to transmit the patient-specific parameters, if necessary after processing them, to an output apparatus and/or to the one or more medical devices, for example by radio, Bluetooth, Wifi or similar, or via an interface located at the stretcher support.

An electrical connection between the temperature-regulating layer, at least one of the one or more sensors, the one or more medical devices, the battery, and the regulation circuit is preferably led within the stretcher support. Due to the leading of the cabling of the electrical components of the stretcher support within the stretcher support, said electrical components can be better protected against external influences.

The electrical connection is preferably led through a transition that is arranged between the head part and the body part. It can thus be ensured that the cabling of the electrical components of the stretcher support is also protected in the region of the transition from the head part to the body part.

The one or more sensors and/or the one or more medical devices is/are particularly preferably connected to the microcontroller. Thus, the patient-specific parameters can be evaluated directly at the stretcher support or can be processed such that a patient located on the stretcher support can be treated.

The one or more sensors and/or the one or more medical devices is/are preferably arranged in the body part or is/are led out of it so that they can be connected to the patient. The shortest measurement path for the various measurable patient-specific parameters is created in this respect. Also, no cables that can, for example, negatively affect medical personnel in emergency situations have to be led from a side wall of the vehicle to the patient, for example.

The one or more sensors and/or the one or more medical devices is/are preferably configured to perform a measurement of the patient-specific parameters and/or a treatment through the stretcher support. A cabling effort within a vehicle can hereby be reduced even further.

It is preferred if the apparatus, in particular the screen of the apparatus, is configured to display the patient-specific parameters. The various measurable patient-specific parameters can thus be displayed directly at the stretcher support.

The output apparatus is preferably a separate output apparatus at which the patient-specific parameters can be displayed and/or by which the patient-specific parameters can be evaluated. For example, the ECG located in the vehicle can be used to display the parameters that are, for example, measured by ECG electrodes that are integrated in the stretcher support. The further parameters can be displayed at parameter-specific units and/or also at a central unit in the vehicle.

The one or more sensors is/are particularly preferably configured to detect parameters that comprise an ECG signal; a pulse; an oxygen value; a temperature; a MetHb value; a sugar value; and/or a CO value of a patient who is placed and/or lies on the stretcher support. In general, the one or more sensors can be configured to record a vital parameter of a patient who is in contact with the support and to make it available for a further processing.

The one or more medical devices preferably comprises/comprise a defibrillator; an oxygen supply; and/or a suction and/or flushing apparatus. They are examples of medical devices that are frequently used in vehicles.

The temperature-regulating stretcher support can preferably be controlled and/or regulated by a smart device such as, for example, a smart phone, a tablet, a smart watch and/or smart glasses, with preferably the patient-specific parameters being able to be displayed and/or evaluated at the smart device in order, if necessary, to perform a control of the temperature-regulating stretcher support (10). Thus, a driver of the vehicle can, for example, adjust the temperature of the stretcher support in dependence on the patient and/or can adjust his manner of driving on the way to a medical facility in dependence on the measured parameters and/or to adjust a medical treatment on the patient in dependence on the measured parameters.

In accordance with a particularly preferred embodiment, the apparatus regulates the temperature of the stretcher support to an at least substantially constant temperature for a duration of 20 to 60 minutes. The duration of 20 to 60 minutes is sufficient to at least be able to perform first aid in mobile use. The duration of the use at a specific temperature can be determined by the selected battery.

The compartment preferably comprises a battery housing and the battery can be removed from said battery housing and can be repeatedly inserted into said battery housing. An electrical connection between the battery and the electronic components of the stretcher support can be improved by such a battery housing and protection against penetration of a liquid into the stretcher support can be improved by such a battery housing.

The battery housing preferably comprises a multi-part housing that is at least liquid-repellent, preferably liquid-tight. Since the battery housing can be configured as liquid-repellent, an entry of liquid into the battery housing can be avoided so that the risk of a short circuit in one or more electronic components, which can be arranged in the stretcher support, can be minimized.

The apparatus is preferably arranged at an outer visible side of the battery housing. The apparatus can thus be arranged at a stable frame so that the risk of an unwanted break of the apparatus can be minimized.

The battery housing preferably has an upper shell, a lower shell, and a cover, with the upper shell being connected to the lower shell and the cover being releasably coupled to the upper shell and to the lower shell, in particular by a releasable snap-in connection. Such a battery housing can be easily manufactured, enables a simple insertion and removal of the battery, and additionally provides a desired protection against external impairments such as liquid and impacts.

The battery is preferably connected to the cover and the battery can be removed from said battery housing and can be inserted into said battery housing together with the cover. The battery can be more easily accommodated in the battery housing by such a cover.

The cover preferably has a frame in which the battery is arranged. The battery can be inserted into the battery housing repeatedly and in a more precise manner by such a frame.

A seal is preferably arranged between the cover and the upper shell as well as the lower shell. Since the cover is usually arranged at the outer side of the support, the seal usually likewise seals from the outside such that no liquid, such as water, detergent, disinfectant, blood or the like, can enter the stretcher support.

The battery housing and/or the cover is/are preferably manufactured from a plastic, preferably in an injection molding process. The components of the battery housing can hereby be manufactured in a cost-effective and reproducible manner.

The seal is preferably arranged between the cover and a groove of an outer frame, with the outer frame connecting the upper shell to the lower shell. The connection between the housing parts of the battery housing can be improved by such an outer frame.

The apparatus is preferably arranged in the region of the connection between the upper shell and the lower shell, preferably arranged at the outer frame. The apparatus can hereby be particularly securely attached to the battery housing.

The battery housing preferably further comprises a reception space for at least one board on which at least one electronic circuit is provided to communicate with the battery. Such an electronic circuit can thus be arranged more securely in the stretcher support than without such a battery housing.

In accordance with a further aspect, the present invention relates to a medical stretcher support comprising one or more sensors; and/or one or more medical devices; and a microcontroller that is configured to process patient-specific parameters that can be measured by the one or more sensors and/or can be processed by the one or more medical devices.

The advantages that were discussed above in connection with the temperature-regulating stretcher support apply accordingly to the medical stretcher support.

Further embodiments of the invention are set forth in the following description of the Figures and in the dependent claims.

BRIEF DESCRIPTION OF THE DRAWINGS

The invention will be explained in more detail hereinafter with reference to the drawings.

FIG. 1 is a schematic cross-section through a stretcher support in accordance with one embodiment of the invention;

FIG. 2 is a view from above of the stretcher support in accordance with FIG. 1;

FIG. 14 is an exploded drawing of the components of FIG. 11.

DETAILED DESCCRIPTION

Figure 3:
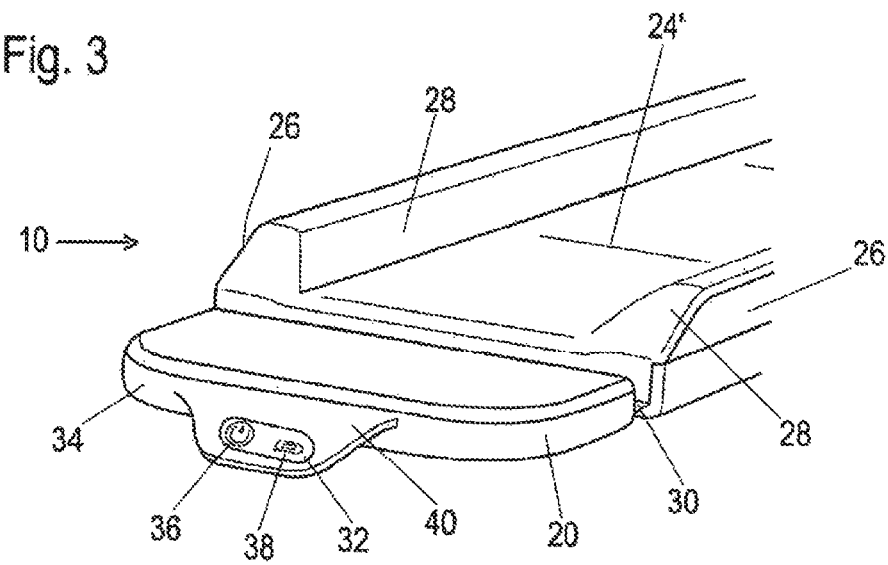
FIG. 3 is a control panel of a further embodiment of a stretcher support.

FIG. 1 shows a schematic cross-section through a stretcher support 10 in accordance with the invention. The stretcher support 10 has a PVC top layer 12 as an outer skin that jackets a heating mat 14 at least regionally. A stabilizing layer 16, which is arranged on a foam body 18, is located beneath the heating mat 14.

The PVC top layer 12 is selected such that it does not allow any moisture to pass through and can be disinfected cost-effectively and quickly in a simple manner. The stabilizing layer 16 is selected such that it prevents a deformation of the heating mat 14 and thus prevents the heating elements (not shown) located therein from breaking through. The stabilizing layer 16 can e.g. be produced from hard foam or other similar material. Furthermore, the stabilizing layer prevents too great a deformation of the temperature-regulating layer so that the latter is more durable and break-resistant.

The foam body 18 disposed thereunder is selected such that a patient transported on it (not shown) is protected from excessive vibrations and can thereby at least enjoy some comfort. The density of the foam body 18 can be individually determined to provide the stretcher support 10 e.g. for the use in a helicopter (not shown). The foam body 18 can e.g. be produced from a cold foam.

In this connection, it should be noted that the layers 14, 16, and 18 described above can also be present in a different arrangement or a layer can be present that takes over the functions of layers 16 and 18 in one layer. Such a layer then forms the support layer 18' of the stretcher support 10.

The stretcher support 10 is in particular suitable for patients with a weight of up to approx. 250 kg, but preferably up to a 120 kg body weight.

The stretcher support 10 can furthermore comprise a waterproof zipper (not shown) that can be arranged at a long side of the outer skin or at the lower side to provide a possibility of replacing or maintaining components of the inner structure, comprising the heating mat; the stabilizing layer; the foam layer; electrical components, etc.

Figure 6:
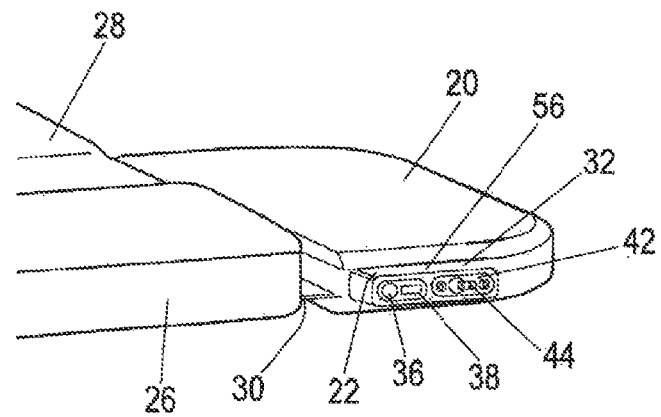
FIG. 6 is a view of the battery of the stretcher support of FIG. 5.

The heating mat 14 forms a temperature-regulating layer 14' that is supplied with power by a battery 22 (see FIG. 6). The temperature-regulating layer 14' can be regulated to an at least substantially constant temperature in the range from 16 to 30° C., in particular from 20 to 30° C., specifically from 22 to 26 to 37° C., wherein the temperature can be set in dependence on the patient by an apparatus 34' (see FIG. 3).

FIG. 2 shows a view from above of a stretcher support 10 in accordance with an embodiment of the invention. The battery 22 (see FIG. 6) is arranged in the head part 20. The heating mat 14 is arranged in the region 24 disposed thereunder, the body part 24' of the stretcher support 10. The region 24 is selected such that the temperature-regulating layer 14 can be regulated to the desired temperature so that the torso (not shown) of a patient can be placed on this temperature-controlled region for a temperature-assisted treatment.

Support regions 28 are respectively disposed at the long sides 26 of the stretcher support 10 to keep a patient supported on the stretcher support 10 within them. The dimensions of the stretcher support 10 can be determined for the required demands in each case.

The temperature-regulated region 24 extends over at least 50% of the surface of the stretcher support 10. The temperature-regulated region 24 preferably extends over 50 to 90% of the surface of the stretcher support 10. It should be noted that the surface of the stretcher support 10 is defined as the region that is bounded by support regions 28 and by the head part 20.

The temperature-regulated region 24 is located in a body part 24' that is coupled to the head part. This coupling takes place in a transition 30.

FIG. 3 shows a control panel 34 of the apparatus 34' of a further embodiment of the stretcher support 10. The apparatus 34' is arranged at the head part 22 of the stretcher support 10. The control panel comprises an on/off button 36 and a charge state display 38. The apparatus 34' is arranged at a lug 40 that is connected to the head part 22.

Figure 4:
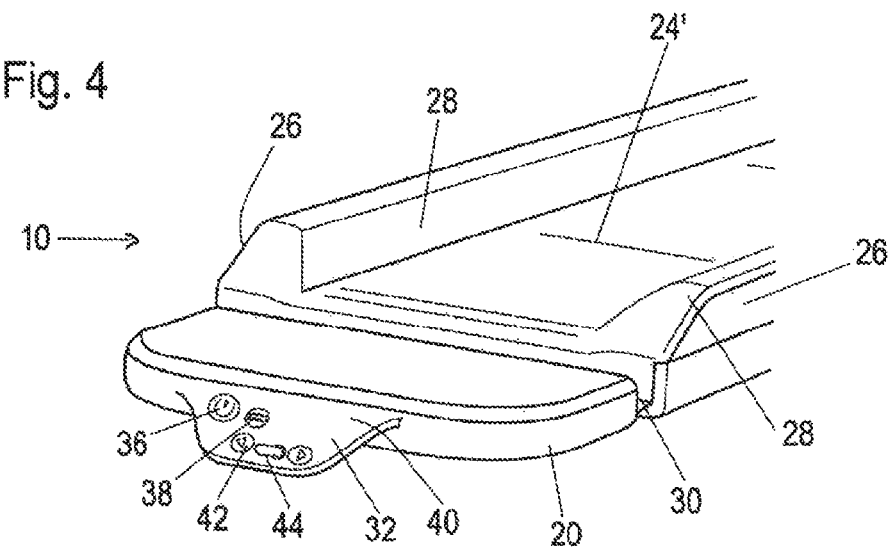
FIG. 4 is a control panel of a further embodiment of a stretcher support.

FIG. 4 shows a further control panel 34 of a further stretcher support 10. In addition to the on/off button 36 and the charge state display 38, the control panel 34 comprises a control panel 42 comprising a temperature display 44 for regulating the temperature of the stretcher support 10.

Figure 5:
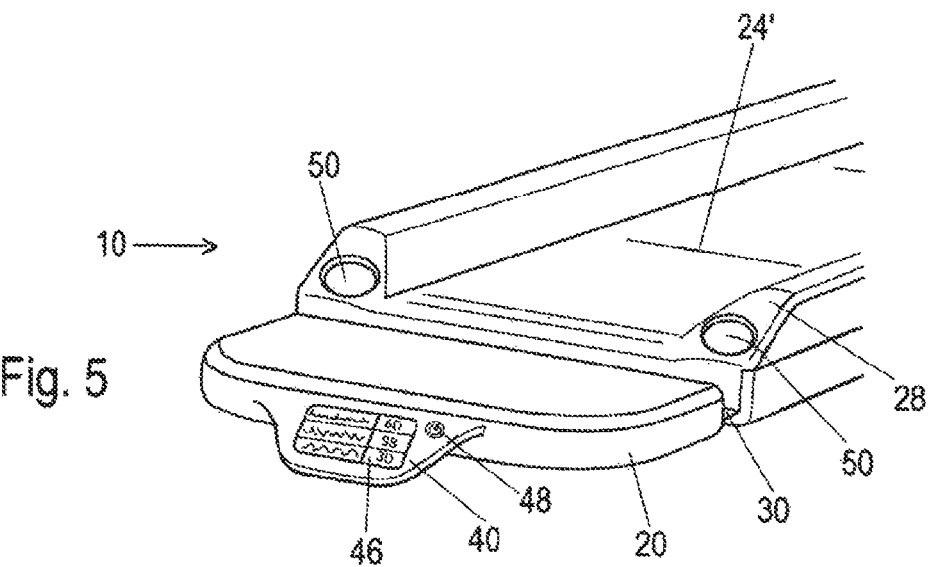
FIG. 5 is a control panel of a further embodiment of a stretcher support.

FIG. 5 shows a screen 46 that is arranged at the lug 40. In the example shown, screen 46 displays an ECG signal that can be measured by a patient (not shown). Furthermore, a knob 48 is visible by which it is possible to switch between different displays of the screen 46 in order to display various patient-specific parameters on the screen 46.

The side parts 28 of FIG. 5 each show an opening 50 of a cable leadthrough through which, for example, ECG cables can be led out of the left cable leadthrough in FIG. 5 to be connected to a patient. An oxygen sensor can, for example, be led out of the right cable leadthrough in FIG. 5 to be connected to the patient. As described in the following example of FIG. 7, the stretcher support 10 can have sensors 52 and 54.

FIG. 6 shows a view of the battery 22 of the stretcher support 10 of FIG. 5. The apparatus 32 is arranged at the battery and comprises a charge state display 38; an on/off button 36; and a control panel 42 for regulating the temperature whose setting can be read off at the temperature display 44.

The battery 22 is arranged in a compartment 56 of the stretcher support 10 in a removable and reinsertable manner. The compartment 56 and the battery 22 are located in the head part 20 of the stretcher support 10. The compartment 56 is adapted to the outer shape of the battery 22 and the stretcher support 10 has a mechanism of means (not shown) for releasably holding the battery 22 in the compartment 56.

Figure 7:
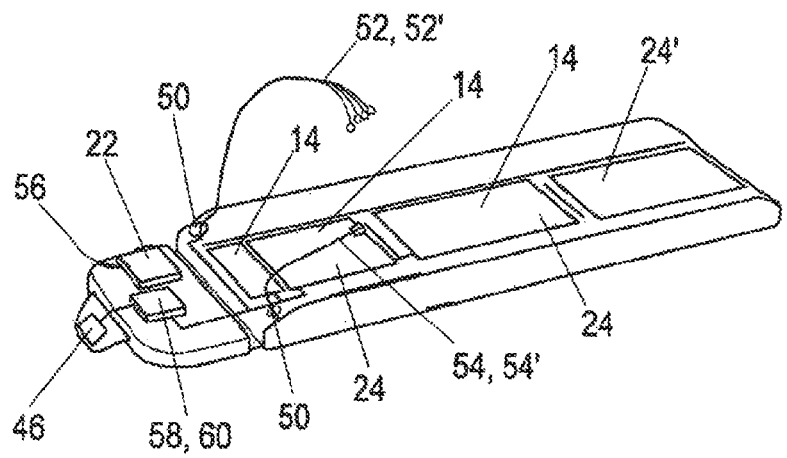
FIG. 7 is a schematic view of the stretcher support of FIG. 5.

FIG. 7 shows a schematic view of the stretcher support 10 of FIG. 5. In the present example, three heating mats 14 are arranged in the body part 24' and together form the temperature-regulated region 24 of the stretcher support 10. The heating mats 14 are each connected to a regulation circuit 56 comprising a microcontroller 58. The regulation circuit is furthermore connected to the battery 22 as the power supply. Patient-specific parameters are measured of two sensors 52, 54; they can be processed or evaluated by the microcontroller 58 and can be transmitted by it to the screen 46 and can be displayed there.

An electrical connection between the temperature-regulating layer 14', the sensors 52, 54, the battery 22, the screen 46, and the regulation circuit 58 is led within the stretcher support 10. Since the battery 22 and the regulation circuit 58 are arranged in the head part 20, the electrical connection between the regulation circuit 58 and the temperature-regulating layer 14', or from the head part 20 to the body part 24', is led through the transition 30 that is arranged between the head part 20 and the body part 24'.

Further or other sensors than the sensors 52, 54 can be integrated in the stretcher support 10. For example, such sensors can be configured to detect parameters that comprise a pulse; a temperature; a MetHb value; and/or a CO value of a patient who is placed and/or lies on the stretcher support.

In addition to or as an alternative to the one or more sensors, one or more medical devices 52', 54' could also be arranged in the stretcher support 10. Depending on the patient-specific parameters, they can be configured to treat the patient, for example, to resuscitate a patient by a defibrillator in the event of a cardiac arrest. The one or more medical devices 52', 54' could, for example, comprise a defibrillator; an oxygen supply; and/or a suction and/or flushing apparatus or similar.

The patient-specific parameters can be transmitted by the microcontroller 60 to a separate output apparatus (not shown) where they can be displayed and/or evaluated.

The patient-specific parameters can also be transmitted to the one or more medical devices by the microcontroller 60 in order to perform a treatment at the patient by the medical device 52', 54' in dependence on the measured patient-specific parameters.

For example, the temperature-regulating stretcher support 10 can be additionally controlled and/or regulated by a smart device (not shown), such as a smartphone, a tablet, a smart watch and/or smart glasses, as a separate output apparatus, wherein the patient-specific parameters can preferably be displayed and/or evaluated at the smart device. The smart device can have a specifically programmed app for these functions. A treatment that is, for example, performed by the medical device 52', 54' can also be controlled by such a smart device, for example.

Figure 8:
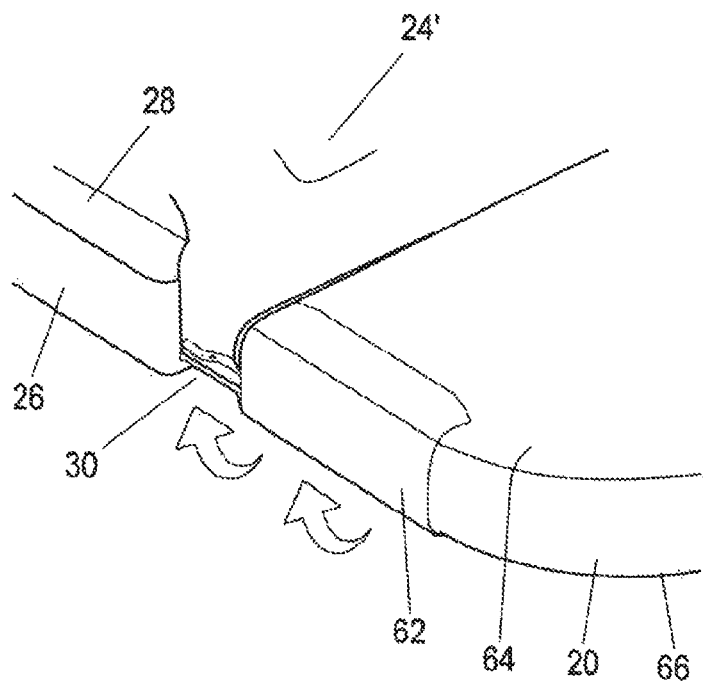
FIG. 8 is a side view of the stretcher support in accordance with FIG. 4.

FIG. 8 shows a side view of the stretcher support 10 in accordance with FIG. 4. The compartment 56 has a covering 62 that is fixedly connected to an upper side 64 of the stretcher support 10 and that is releasably connected to the lower side 66 of the stretcher support 10.

For example, a magnetic tape (not shown) can be worked in at the covering 62 and cooperates with a magnetic counter-piece at the lower side 66 of the stretcher support 10 to keep the covering in use. The covering 62 is released from the lower side 66 during use and is recessed relative to the upper side to enable access to the compartment 56 and to the battery 22. When the stretcher support 10 is used, the upper side 64 corresponds to the side on which the patient is arranged.

Figure 9:
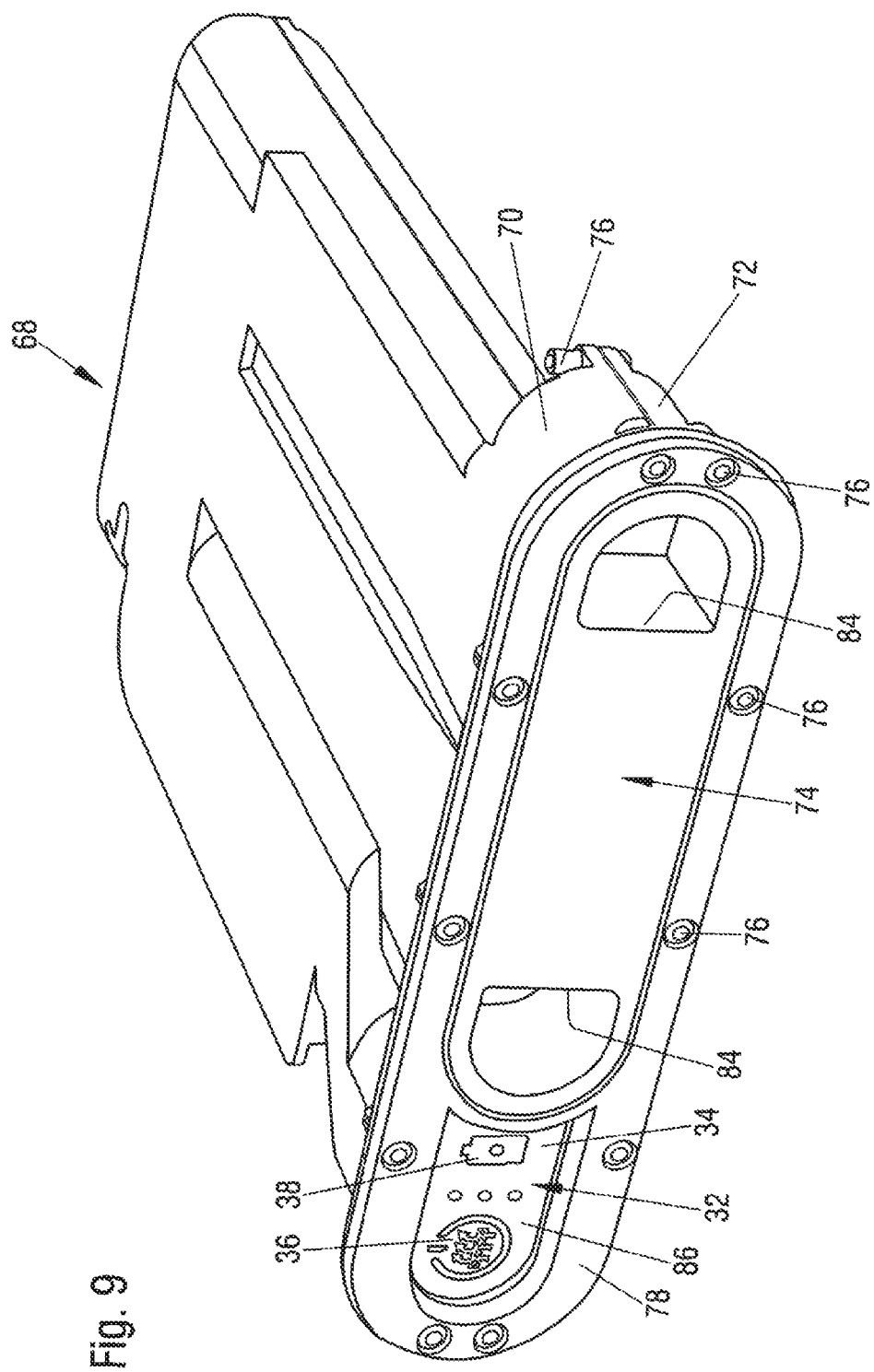
FIG. 9 is a view of a battery housing.

FIG. 9 shows a view of a battery housing 68. The battery housing 68 is fixedly installed in the compartment 58. The battery 22 can both be removed from and inserted back into said battery housing 68, for example, to be charged or maintained externally and separately from the stretcher support 10.

The battery housing 68 is a multi-part housing that is at least liquid-repellent, preferably liquid-tight, to prevent an entry of liquid in the region of the battery into the stretcher support 10.

The battery housing 68 has an upper shell 70, a lower shell 72, and a cover 74, with the upper shell 70 being connected to the lower shell 72. Screw connections 76 are provided to improve the connection between the upper shell 70 and the lower shell 78. Furthermore, an outer frame 78 is connected to the upper shell 70 and to the lower shell 78 by screw connections 76. The screw connection typically comprises a bolt and a nut, but can also be formed by an integral internal thread or external thread that accordingly cooperate with a bolt or a nut.

On the assembly, the cover 74 is inserted through the outer frame 78 into a reception space 80, which is formed between the upper shell 70 and the lower shell 72 (see FIGS. 12 and 13), and is releasably coupled to the upper shell 70 and to the lower shell 72.

Figure 12:
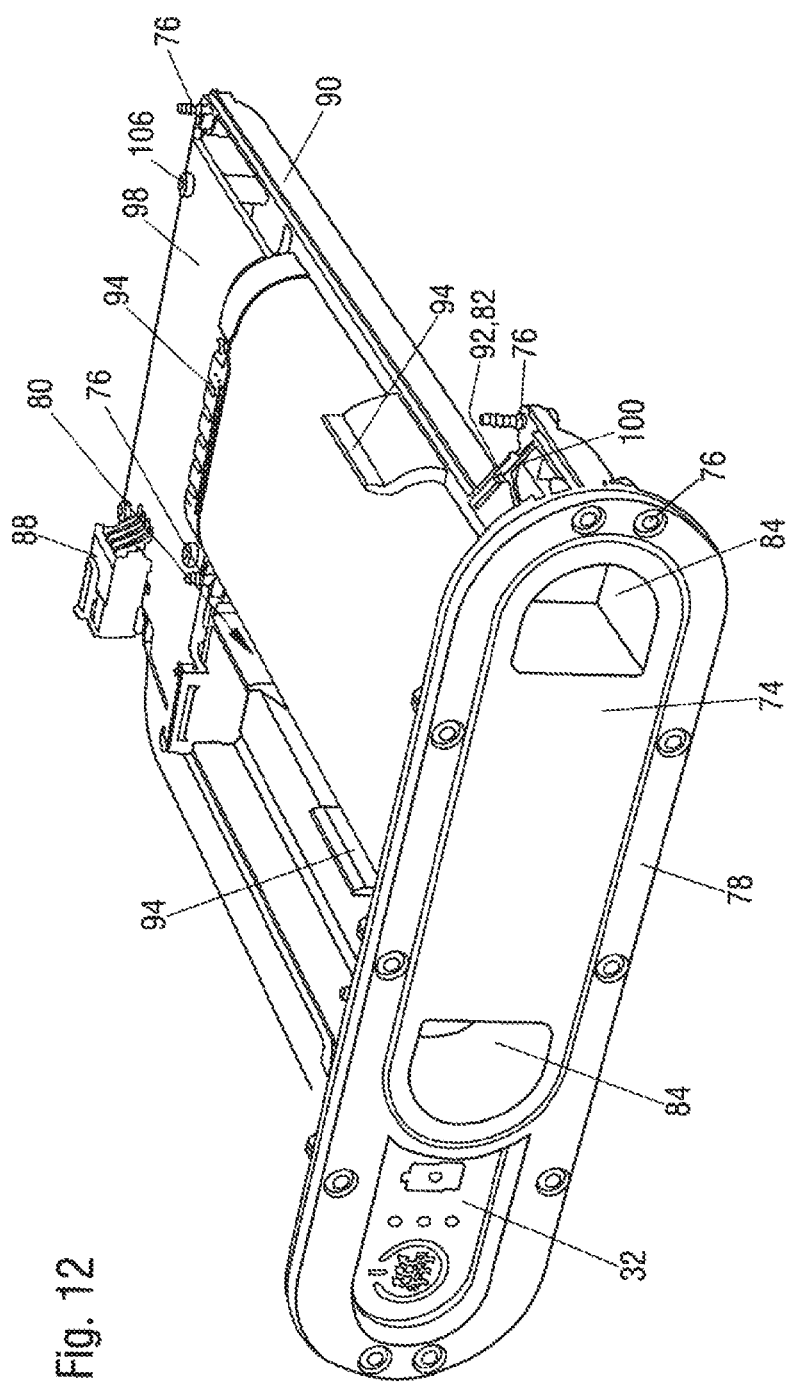
FIG. 12 is a view of the battery housing of FIG. 9 in which an upper shell has been removed.

The coupling between the frame and the upper shell 70 as well as the lower shell 72 is made possible by a releasable snap-in connection 82 (see FIG. 12). The snap-in connection 82 can be activated by a pressing in the recesses 84 to release the connection, for example.

The apparatus 32 is arranged at an outer visible side of the battery housing 68. This takes place in that a film circuit 86, on which the control panel 34 comprising the on/off button 36 and the charge state display 38 is arranged, is fastened to the upper shell 70, to the lower shell 72, and, if necessary, to the frame 78.

Figure 10:
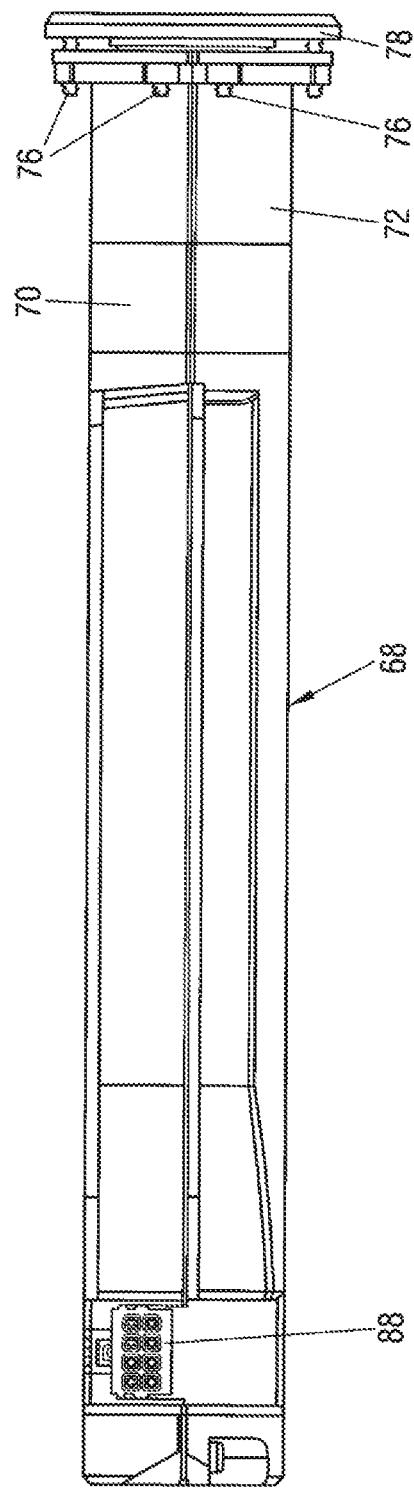
FIG. 10 is a side view of the battery housing of FIG. 9.

FIG. 10 shows a side view of the battery housing 68. An electrical interface 88 is disposed at the rear end of the battery housing 68 that is disposed opposite the frame 78. The electronic components of the stretcher support 10, such as the heating mat 14, the regulation circuit 58, the microcontroller 60, the sensors 52, 54, and the medical devices 52', 54', can be supplied with power by this interface 88.

Figure 11:
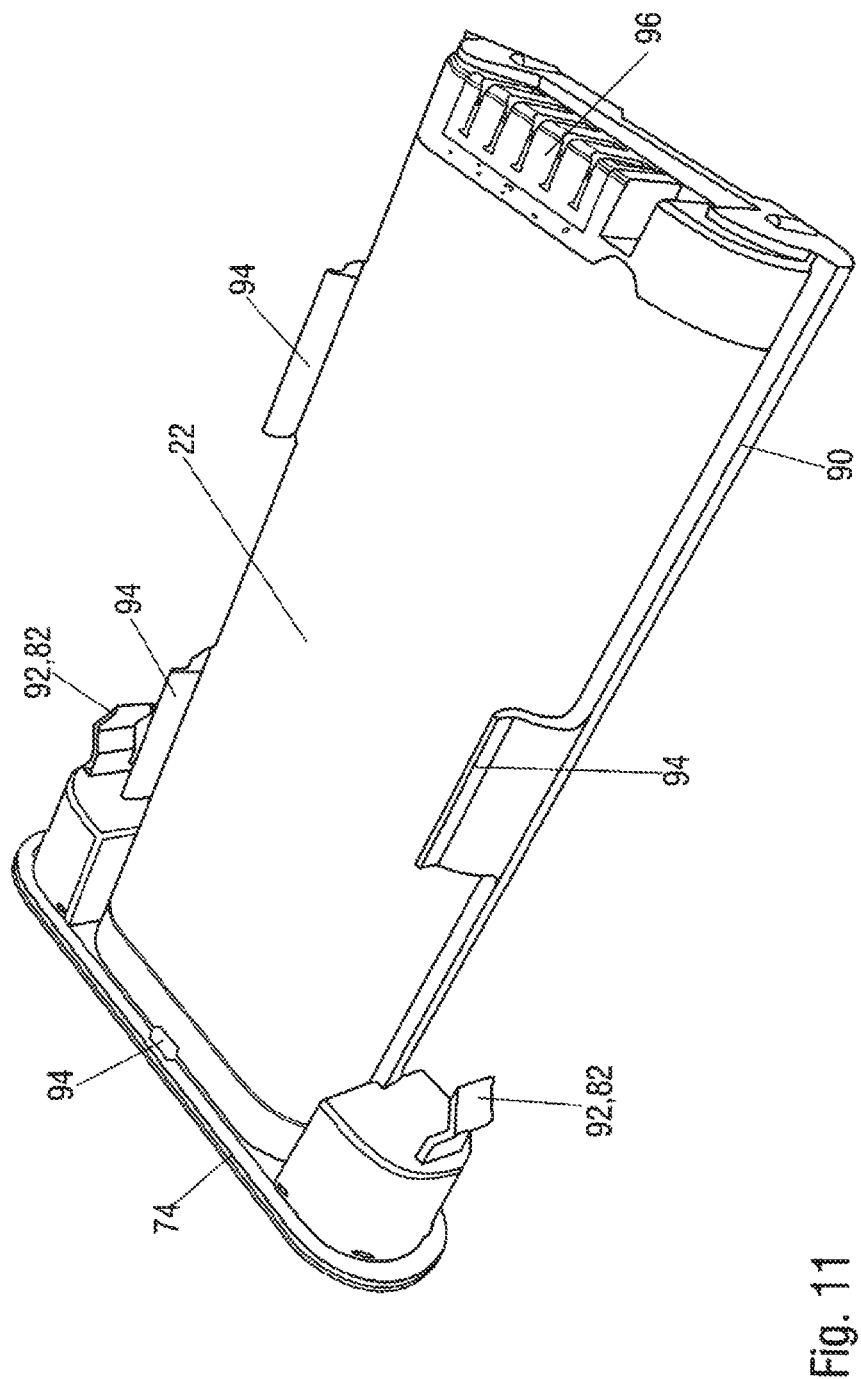
FIG. 11 is a view of a battery that is arranged in a frame of the battery housing of FIG. 9.

FIG. 11 shows a view of the battery 22 that is arranged in a frame 90 of the battery housing 68. The frame 90 is fastened to the cover 74 for this purpose. More precisely, the frame 90 together with the cover 74 is manufactured from plastic in an injection molding process.

To connect the cover to the upper shell 70 as well as to the lower shell 72, snap hooks 92 are disposed at one part of the cover 74 at whose oppositely disposed side the cutouts 84 are provided.

The battery 22 is connected in a form-fitting manner to both the cover 74 and the frame 90 by latch noses 94. The battery 22 can be removed from the battery housing 68 together with the cover 74 and the frame 90 and can also be inserted again.

At its end disposed opposite the cover 74, the battery 22 has a battery interface 96 by which the battery 22 can be electronically connected to the interface 88.

FIG. 12 shows a view of the battery housing 68 in which the upper shell 70 has been removed. A board 98 is arranged in the rear end of the battery housing 68 and electronically connects the battery 22 via the battery interface 96 to the interface 88. The board is fastened to the lower shell 72 by screws 106, for example.

Furthermore, two cutouts 100 are disposed at the front end of the battery housing 68 and are configured to interact with the snap hooks 92. In FIG. 12, one of these cutouts 100 is covered by the outer frame 78 so that it is not visible.

Figure 13:
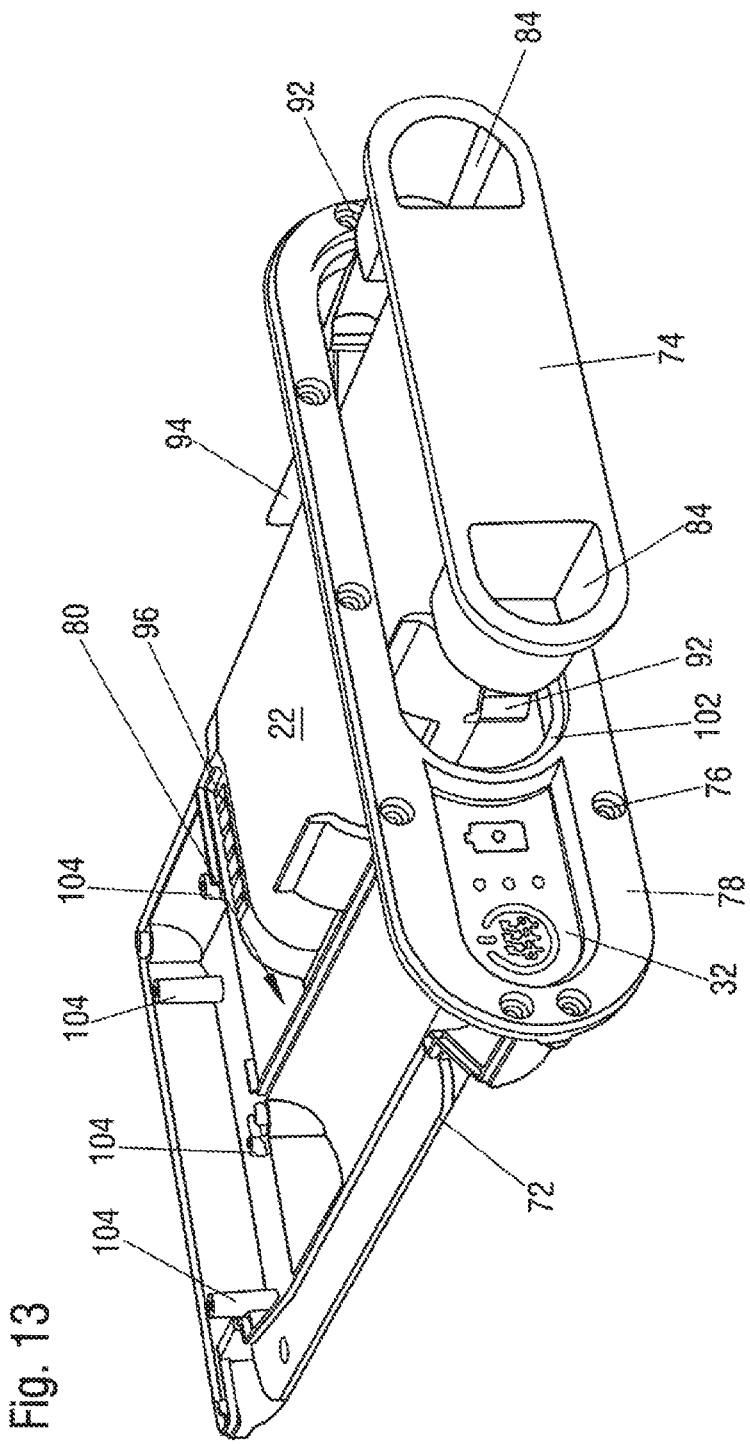
FIG. 13 is a view of the battery housing of FIG. 12 in which a board has been removed and the battery is not completely arranged in the battery housing.

FIG. 13 shows a view of the battery housing 68 in which the board 98 and the interface 88 have been removed and in which the battery 22 has been slightly pulled out of the battery housing 68. At the rear end of the battery housing 68, webs 104 are visible by which the board 98 can be fastened to the lower shell 72 by the screws 106.

The outer frame 78 has a groove 102 which the cover 74 contacts when the battery 22 is inserted.

FIG. 14 shows an exploded drawing in which the battery 22 is removed from the frame 90. The cover 74 has an inner side 108 that forms a planar surface. A seal 110 can likewise be seen that is arranged at this inner side 108 by pulling it onto the frame 90 in the direction of the arrow 112. This seal 110 enables a sealing between the cover 74, the upper shell 70, and the lower shell 72.

The upper shell 70, the lower shell 72, and the cover 74 are manufactured from a plastic, in particular a thermoplastic, preferably in an injection molding process. For example, the thermoplastic can be selected from the following list of thermoplastics: acrylonitrile butadiene styrene (ABS), polyamides (PA), polylactide (PLA), polymethyl methacrylate (PMMA), polycarbonate (PC), polyethylene terephthalate (PET), polyethylene (PE), polypropylene (PP), polystyrene (PS), polyetheretherketone PEEK polyvinyl chloride (PVC).

The battery housing 68 is fixedly connected to the stretcher support 10 and is arranged in the compartment 56. The snap-in connection 82 is provided to prevent the battery 22 from flying out of the battery housing. In addition to the snap-in connection 82, the battery 22 can also be held in the compartment 56 by the covering 62 such as is, for example, shown in FIG. 8.

The invention claimed is:

1. A temperature-regulating support, comprising: a head part; a body part coupled to the head part; at least one temperature-regulating layer configured to be regulated to an at least substantially constant temperature in a range from 15 to 42° C. with the temperature capable of being set in dependence on a patient by an apparatus and a support layer, the at least one temperature-regulating layer having a battery as a power supply, the battery configured to be arranged in a compartment of the support so as to be capable of being removed from the compartment and inserted into the compartment; and the apparatus is arranged at the battery; and a battery housing having an upper shell, a lower shell, and a cover, with the upper shell being connected to the lower shell and the cover being releasably coupled to the upper shell and to the lower shell by a releasable snap-in connection, and a seal disposed on the upper shell and the lower shell, such that the seal is configured to contact the cover when the cover is snapped in to the upper and lower shells, and the seal is configured to be disengaged from the cover when the cover is released from the upper and lower shells.

2. The temperature-regulating support in accordance with claim 1, wherein
the compartment and the battery are arranged in the head part.

3. The temperature-regulating support in accordance with claim 1, wherein the compartment is configured in a outer shape of the battery and the temperature-regulating support and, the apparatus is arranged at the temperature-regulating support.

4. The temperature-regulating support in accordance with claim 1,
wherein the apparatus is arranged at the head part of the temperature-regulating support.

5. The temperature-regulating support in accordance with claim 1,
wherein
the apparatus comprises at least one of a charge state display, an on/off button, a control panel for regulating the temperature, a temperature display, or a screen.

6. The temperature-regulating support in accordance with claim 1,
wherein the apparatus is connected to the battery, to the temperature-regulating layer, and to a regulation circuit.

7. The temperature-regulating support in accordance with claim 6,
wherein the regulation circuit comprises a microcontroller.

8. A medical support comprising:
a temperature-regulating support comprising a head part and a body part coupled to the head part; at least one temperature-regulating layer, and a support layer, the at least one temperature-regulating layer having a battery as a power supply, the battery arranged in a compartment of the support, and the battery capable of being removed from the compartment and inserted into the compartment;
one or more sensors or one or more medical devices;
a microcontroller configured to process patient-specific parameters that are measured by the one or more sensors or processed by the one or more medical devices; and
a battery housing having an upper shell, a lower shell, and a cover, with the upper shell being connected to the lower shell and the cover being releasably coupled to the upper shell and to the lower shell by a releasable snap-in connection, and a seal disposed on the upper shell and the lower shell, such that the seal is configured to contact the cover when the cover is snapped-in to the upper and lower shells, and the seal is configured to be disengaged from the cover when the cover is released from the upper and lower shells.

9. The medical support in accordance with claim 8, wherein
the battery is connected to at least one of the one or more sensors or the one or more medical devices.

10. The medical support in accordance with claim 8, wherein
the medical support is capable of being controlled or regulated by a smart device, with the patient-specific parameters being able to be displayed or evaluated at the smart device control the temperature-regulating support.

11. A temperature-regulating support, comprising:
a head part;
a body part coupled to the head part;
at least one temperature-regulating layer; and
a support layer,
the at least one temperature-regulating layer having a battery as a power supply, the battery arranged in a compartment of the support, the battery capable of being removed from the compartment and inserted into compartment,
the compartment comprising a battery housing, and capable of being removed from the battery housing and inserted into the battery housing, and
the battery housing comprising a multi-part housing that is at least liquid-repellent, the battery housing having an upper shell, a lower shell, and a cover, with the upper shell being connected to the lower shell and the cover being releasably coupled to the upper shell and to the lower shell by a releasable snap-in connection, and a seal disposed on the upper shell and the lower shell, such that the seal is configured to contact the cover when the cover is snapped-in to the upper and lower shells, and the seal is configured to be disengaged from the cover when the cover is released from the upper and lower shells.

12. The temperature-regulating support in accordance with claim 11, wherein
the apparatus is arranged at an outer visible side of the battery housing.

13. The temperature-regulating support in accordance with claim 11, wherein
the battery is connected to the cover; and the battery is capable of being removed from the battery housing and inserted into the battery housing together with the cover.

14. The temperature-regulating support in accordance with claim 11,
wherein the cover has a frame in which the battery is arranged.

15. The temperature-regulating support in accordance with claim 11,
wherein the seal is arranged between the cover and a groove of an outer frame, with the outer frame connecting the upper shell to the lower shell.

16. The temperature-regulating support in accordance with claim 11,
wherein at least one of the battery housing or the cover is manufactured from a plastic.

17. The temperature-regulating support in accordance with claim 11,
wherein the apparatus is arranged in a region of a connection between the upper shell and the lower shell.

18. The temperature-regulating support in accordance with claim 11,
wherein the battery housing further comprises a reception space for at least one board on which at least one electronic circuit is provided to communicate with the battery.

19. The temperature-regulating support in accordance with claim 11, wherein at least one of the support or the battery is configured to output an acoustic or visual signal when a predefined charge state threshold is undercut.

* * * * *